United States Patent
Nayani et al.

(10) Patent No.: US 12,280,053 B2
(45) Date of Patent: Apr. 22, 2025

(54) STABLE, READY TO USE AQUEOUS PHARMACEUTICAL COMPOSITION OF PEMETREXED

(71) Applicant: INTAS PHARMACEUTICALS LTD., Gujarat (IN)

(72) Inventors: Anil Nayani, Ahmedabad (IN); Mukesh Bothra, Ahmedabad (IN); Alex George, Ahmedabad (IN)

(73) Assignee: Intas Pharmaceuticals Ltd., Ahmedabad (IN)

( * ) Notice: Subject to any disclaimer, the term of this patent is extended or adjusted under 35 U.S.C. 154(b) by 783 days.

(21) Appl. No.: 17/605,796

(22) PCT Filed: Apr. 30, 2020

(86) PCT No.: PCT/IB2020/054063
§ 371 (c)(1),
(2) Date: Oct. 22, 2021

(87) PCT Pub. No.: WO2020/222151
PCT Pub. Date: Nov. 5, 2020

(65) Prior Publication Data
US 2022/0211709 A1    Jul. 7, 2022

(30) Foreign Application Priority Data
May 1, 2019  (IN) .............................. 201921017365

(51) Int. Cl.
| | | |
|---|---|---|
| C07D 487/04 | (2006.01) | |
| A61K 9/00 | (2006.01) | |
| A61K 9/08 | (2006.01) | |
| A61K 31/519 | (2006.01) | |
| A61K 47/12 | (2006.01) | |
| A61K 47/20 | (2006.01) | |
| A61P 35/00 | (2006.01) | |

(52) U.S. Cl.
CPC .......... *A61K 31/519* (2013.01); *A61K 9/0019* (2013.01); *A61P 35/00* (2018.01)

(58) Field of Classification Search
CPC .. C07D 487/04; A61K 31/519; A61K 9/0019; A61K 9/08; A61K 47/12; A61K 47/20; A61P 35/00
See application file for complete search history.

(56) References Cited

U.S. PATENT DOCUMENTS

| | | |
|---|---|---|
| 5,344,932 A | 9/1994 | Taylor |
| 5,416,211 A | 5/1995 | Barnett et al. |
| 6,262,262 B1 | 7/2001 | Kjel |
| 6,686,365 B2 | 2/2004 | Riebesehl et al. |
| 10,391,052 B2 * | 8/2019 | Hashimoto .......... A61K 31/519 |
| 2018/0235969 A1 | 8/2018 | Zaludek |

FOREIGN PATENT DOCUMENTS

| | | |
|---|---|---|
| WO | 2008/021410 | 2/2008 |
| WO | 2012/015810 | 2/2012 |
| WO | 2012/121523 | 9/2012 |
| WO | 2013/144814 | 10/2013 |
| WO | 2013/179310 | 12/2013 |
| WO | 2014/060962 | 4/2014 |
| WO | 2014/167585 | 10/2014 |
| WO | 2016/207443 | 12/2016 |

OTHER PUBLICATIONS

International Search Report issued in International Application No. PCT/2020/054063, Aug. 6, 2020, 3 pages.
Written Opinion of the International Searching Authority issued in International Application No. PCT/2020/054063, Aug. 6, 2020, 5 pages.

* cited by examiner

*Primary Examiner* — Brenda L Coleman
(74) *Attorney, Agent, or Firm* — HSML P.C.

(57) ABSTRACT

The present invention provides a stable, ready to use aqueous parenteral composition comprising Pemetrexed, wherein the composition comprises Pemetrexed disodium, mixture of antioxidants and pharmaceutically acceptable excipients. Further the present invention provides process for preparation of said composition.

8 Claims, No Drawings

STABLE, READY TO USE AQUEOUS PHARMACEUTICAL COMPOSITION OF PEMETREXED

RELATED APPLICATION

This application is related to Indian Provisional Application No. IN201921017365 filed on 1 May 2019 and is incorporated herein in its entirety.

FIELD OF THE INVENTION

The present invention relates to a stable, ready to use aqueous parenteral composition comprising Pemetrexed and pharmaceutically acceptable excipients. Further present invention discloses process for the preparation of the said composition.

BACKGROUND OF THE INVENTION

Pemetrexed has the chemical name (2S)-2-{[4-[2-(2-amino-4-oxo-1,7-dihydro pyrrolo[2,3-d]pyrimidin-5-yl)ethyl]benzoyl]amino}-pentanedioic acid. The structural formula of the Pemetrexed is shown in Formula (I).

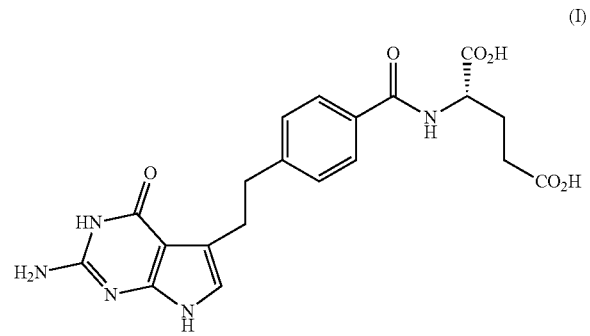 [SMILES: Nc1nc2[nH]cc(CCc3ccc(C(=O)N[C@@H](CCC(=O)O)C(=O)O)cc3)c2c(=O)[nH]1]

Pemetrexed is used in the treatment of malignant pleural mesothelioma and non-small cell lung cancer. Pemetrexed disodium heptahydrate is marketed by Eli Lilly and Company under the trade name ALIMTA® and is supplied as a sterile lyophilized powder for intravenous infusion available in single-dose vials containing 100 mg or 500 mg equivalent Pemetrexed. During July 2004, the drug was approved by the FDA as a second line agent for the initial treatment of advanced or metastatic non-small cell lung cancer. The product formulation contains in addition to the active ingredient, mannitol and may contain hydrochloric acid and/or sodium hydroxide to adjust pH of the formulation.

Pemetrexed is in the class of chemotherapy drugs called folate antimetabolites. By inhibiting thymidylate synthase (TS), dihydrofolate reductase (DHFR), and glycinamide ribonucleotide formyl transferase (GARFT), and hence the formation of precursor purine and pyrimidine nucleotides, Pemetrexed prevents the formation of DNA and RNA, which are required for the growth and survival of both normal cells and cancer cells.

Pemetrexed was first disclosed in U.S. Pat. No. 5,344,932 patent, which provides that the compounds claimed therein, can be administered parenterally.

Pemetrexed diacid and its preparations were disclosed in U.S. Pat. Nos. 5,416,211, 6,262,262, and WO2008021410.

U.S. Pat. No. 6,686,365 patent discloses ready to use (RTU) formulations of Pemetrexed, which contain monothioglycerol, L-cysteine or thioglycolic acid. The US'365 patent also discloses that the formulations which can be stored at room temperature are desirable. However, Pemetrexed containing formulations having one of monothioglycerol, L-cysteine or thioglycolic acid as referred to in the US'365 patent when included at their recommended concentrations of 2.4 mg/ml, together with Pemetrexed at a concentration of 25 mg/ml failed to demonstrate sufficient long-term stability. The drug content fell well below the acceptable levels.

PCT patent application WO2012/015810 discloses a long term, storage stable liquid pharmaceutical composition comprising Pemetrexed, antioxidants like lipoic acid, dihydrolipoic acid, methionine, and mixtures thereof; a chelating agent selected from lactobionic acid, sodium citrate tribasic and mixtures thereof; pH adjusting/modifying agents and pharmaceutically acceptable fluid.

PCT patent application WO2013/179310 claims a storage stable concentrated aqueous parenteral composition comprising Pemetrexed disodium and at least one stability enhancing adjuvant such as cyclodextrin derivatives and method of preparing such compositions. The formulations claimed in WO2013/179310 were shown to be stable at refrigerate temperature (2 to 8° C.).

PCT application publication WO2012/121523 describes method for preparing a pharmaceutical formulation in the form of solution for injection without antioxidant. The method comprises of: (a) controlling a dissolved oxygen concentration in a solution for injection comprising Pemetrexed or its salt to 1 ppm or less; and (b) filling a container for injection with the solution obtained from the step (a), in a closed system having an oxygen partial pressure of 0.2% v/v or less. The WO2012/121523 publication teaches various degassing methods to reduce dissolved oxygen level in finished formulation.

PCT application publication WO2013/144814 describes a liquid pharmaceutical composition comprising Pemetrexed or pharmaceutically acceptable salts thereof, wherein the composition is free from antioxidants, amino acids and chelating agents.

PCT application publication WO2014/167585 describes stable formulations of Pemetrexed for infusion. The formulations are based on using Pemetrexed diacid and certain selected suitable stabilizing basic amine compounds. The suitable basic amine addition compounds according to the invention are one or more of diethanolamine, tris-(hydroxymethyl) aminomethane and meglumine.

A stable, ready to use solution is particularly desired for a pharmaceutical formulation such as Pemetrexed, wherein such ready to use formulation provides easier, safer handling, storage, and distribution. It is particularly desirable if the stable formulation can be prepared without the use of freeze drying techniques. The desired liquid formulation can offer enhanced safety for caregiver handling of the cytotoxic materials. Further, a stable, ready to use formulation is more acceptable to the patient/healthcare provider.

It was discovered that a simple, isotonic saline solution of Pemetrexed is not pharmaceutically acceptable for commercial purposes due to degradation of the solution to form unacceptable related substances. The chemical instability of Pemetrexed is mainly attributed to their oxidative degradation. Hence, the main challenge lies in formulating a stable pharmaceutical composition of Pemetrexed that has the minimum concentration of oxidative degradation impurities.

Formulating a liquid composition of Pemetrexed is particularly challenging because of the tendency of Pemetrexed to degrade. This problem is especially exacerbated when Pemetrexed is present in solution, as its degradation or discoloration occurs much more readily due to oxidation or hydrolysis. The degradation on storage of Pemetrexed can lead to a significant visible color change which leads to lesser patient compliance.

More specifically, it is challenging to produce stable aqueous parenteral product of Pemetrexed at large or commercial scale and devoid of any particulate matter during storage.

Stress stability studies for Pemetrexed have shown that there are two main degradation pathways. In solid state Pemetrexed undergo oxidation while in solution it degrades via hydrolysis. This rapid degradation in solution state is one of the main factors that have prevented aqueous Pemetrexed formulations having long-term stability from being commercially available. In solution state under acidic condition decarboxylation of glutamic acid is observed, while under alkaline condition degradation proceeds by side chain amide hydrolysis followed by deamination and in presence of oxygen Pemetrexed undergoes oxidative degradation.

The relatively rapid formation of degradants is one of the factors which have prevented aqueous Pemetrexed formulations having long-term stability from being commercially available. Five major degradants of Pemetrexed have been observed. Under acidic conditions, decarboxylation of glutamic acid is observed. Under alkaline conditions, degradation proceeds by side chain amide hydrolysis followed by deamination. In the presence of oxygen, two oxidative degradants result. It has shown to be a challenge to formulate Pemetrexed due to stability issues. New alternative Pemetrexed formulations with improved stability would be appreciated.

Therefore, the present invention provides stable, ready to use aqueous parenteral composition of Pemetrexed comprising Pemetrexed disodium, antioxidants, an aqueous vehicle and optional additives like pH modifiers and buffering agents, wherein Pemetrexed exhibits stability in such aqueous solutions.

OBJECTS OF THE INVENTION

The principal object of this invention is to provide a stable, ready to use aqueous parenteral composition comprising Pemetrexed and pharmaceutically acceptable excipients.

Another object of the present invention is to provide a process for preparation of a stable, ready to use aqueous parenteral composition comprising Pemetrexed and pharmaceutically acceptable excipients.

Yet another object of the present invention is to provide a stable, ready to use aqueous parenteral composition comprising Pemetrexed, wherein;
(1) Pemetrexed is in form of Pemetrexed disodium, and
(2) Pharmaceutical composition comprising mixture of antioxidants and pharmaceutically acceptable excipients.

Yet another object of the present invention is to provide a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants and pharmaceutically acceptable excipients.

Yet another object of the present invention is to provide a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants, wherein amount of antioxidants is between of 2.5-6 mg/ml Yet another object of the present invention is to provide a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants, where in the antioxidants are a mixture of monothioglycerol and methionine.

Yet another object of the present invention is to provide a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants, wherein the antioxidants are a mixture of monothioglycerol and methionine, wherein amount of monothioglycerol is 3-6 mg/ml and methionine is 0.5 mg/ml.

Yet another object of the present invention is to provide a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants, wherein the antioxidants are a mixture of monothioglycerol and methionine, wherein amount of monothioglycerol is 4.4 mg/ml and methionine is 0.5 mg/ml.

Yet another object of the present invention is to provide a stable, ready to use aqueous parenteral composition comprising Pemetrexed disodium, wherein the pH of the composition is between 6-9 and more preferably between 7-8.5.

Yet another object of the present invention is to provide a stable, ready to use aqueous parenteral composition comprising Pemetrexed disodium, wherein the composition comprises Pemetrexed disodium from 20-30 mg/mL, monothioglycerol 3-6 mg/ml, methionine 0.5 mg/ml and pH of the composition is in between 6-9.

Yet another object of the present invention is to provide a stable, ready to use aqueous parenteral composition comprising Pemetrexed disodium, wherein the composition comprises Pemetrexed disodium 27.57 mg/ml which is equivalent to 25 mg/ml Pemetrexed, monothioglycerol 4.4 mg/ml, methionine 0.5 mg/ml, citric acid anhydrous 15 mg/ml and pH of the composition is in between 7-8.5.

Yet another object of the present invention is to provide a stable, ready to use aqueous parenteral composition comprising Pemetrexed disodium, wherein the composition comprises;
(a) Pemetrexed disodium 27.57 mg/ml which is equivalent to 25 mg/ml Pemetrexed,
(b) Monothioglycerol 4.4 mg/ml,
(c) Methionine 0.5 mg/ml,
(d) Citric acid anhydrous 15 mg/ml,
and pH of the composition is in between 7-8.5, wherein amount of any single unknown impurities of Pemetrexed composition is not more than 0.2% after 6 month stability study at 40° C. and 75% RH, and total impurity of Pemetrexed composition is not more than 2% at any time during self-life of the composition.

SUMMARY OF THE INVENTION

The present invention provides a stable, ready to use aqueous parenteral composition comprising Pemetrexed, wherein the composition comprises Pemetrexed disodium, mixture of antioxidants and pharmaceutically acceptable excipients. Further the present invention provides process for preparation of said composition.

DETAILED DESCRIPTION OF THE INVENTION

The present invention provides a stable, ready to use aqueous parenteral composition of Pemetrexed disodium, mixture of antioxidants and pharmaceutically acceptable excipients. The composition according to the present invention is suitable for ready to use for parenteral administration. i.e. which does not require reconstitution like lyophilized composition.

In another embodiment, the present invention provides a process for preparation of a stable, ready to use aqueous parenteral composition comprising Pemetrexed disodium, mixture of antioxidants and pharmaceutically acceptable excipients.

In another embodiment, the present invention provides a stable, ready to use aqueous parenteral composition comprising Pemetrexed, wherein;
(1) Pemetrexed is in form of Pemetrexed disodium, and
(2) Pharmaceutical composition comprising mixture of antioxidants and pharmaceutically acceptable excipients.

In another embodiment, the present invention provides a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants and pharmaceutically acceptable excipients.

In another embodiment, the present invention provides a stable, ready to use aqueous parenteral composition comprising Pemetrexed disodium and mixture of antioxidants, wherein;
(1) Amount of Pemetrexed disodium is from 2.5 mg/ml to 50 mg/ml and
(2) Amount of mixture of antioxidants is between about 3 mg/ml to about 6 mg/ml.

In another embodiment, the present invention provides a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants, where in amount of antioxidants is between of 2.5-6 mg/ml In another embodiment, the present invention provides a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants, where in the antioxidants are mixture of monothioglycerol and methionine.

In another embodiment, the present invention provides a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants, where in the antioxidants are mixture of monothioglycerol and methionine, wherein amount of monothioglycerol is 3-6 mg/ml and methionine is 0.5 mg/ml.

In another embodiment, the present invention provides a stable, ready to use aqueous parenteral composition comprising Pemetrexed disodium, wherein;
(1) Amount of Pemetrexed disodium is from about 2.5 mg/ml to about 50 mg/ml, and more preferably between 20-30 mg/ml
(2) Pharmaceutical composition comprising mixture of antioxidants, where in the antioxidants are mixture of monothioglycerol and methionine, wherein amount of monothioglycerol is 4.4 mg/ml and methionine is 0.5 mg/ml.

In another embodiment, the present invention provides a stable, ready to use aqueous parenteral composition comprising Pemetrexed disodium, wherein the composition comprises Pemetrexed disodium from 20-30 mg/mL, monothioglycerol 3-6 mg/ml, methionine 0.5 mg/ml and pH of the composition is in between 6-9.

In another embodiment, the present invention provides a stable, ready to use aqueous parenteral composition comprising Pemetrexed disodium, wherein the composition comprises Pemetrexed disodium 27.57 mg/ml which is equivalent to 25 mg/ml Pemetrexed, monothioglycerol 4.4 mg/ml, methionine 0.5 mg/ml, citric acid anhydrous 15 mg/ml and pH of the composition is in between 7-8.5.

In another embodiment, the present invention provides a stable, ready to use aqueous parenteral composition comprising Pemetrexed disodium, wherein the composition comprises;
(a) Pemetrexed disodium 2.5 mg/ml to 50 mg/ml,
(b) monothioglycerol 3 mg/ml to 6 mg/ml,
(c) methionine 0.5 mg/ml,
(d) citric acid,
and pH of the composition is in between 7-8.5.

In another embodiment, the present invention provides a stable, ready to use aqueous parenteral composition comprising Pemetrexed disodium, wherein the composition comprises;
(a) Pemetrexed disodium 27.57 mg/ml which is equivalent to 25 mg/ml Pemetrexed,
(b) monothioglycerol 4.4 mg/ml,
(c) methionine 0.5 mg/ml,
(d) citric acid anhydrous 15 mg/ml,
and pH of the composition is in between 7-8.5,
wherein amount of any single unknown impurities of Pemetrexed composition is not more than 0.2% after 6 month stability study at 40° C. and 75% RH, and total impurity of Pemetrexed composition is not more than 2% at any time during self-life of the composition.

In another embodiment, the present invention provides a process for preparation of a stable, ready to use aqueous parenteral composition comprising Pemetrexed disodium according present invention, wherein the process comprises the steps of:
  (a) Adding citric acid in water for injection,
  (b) Adjusting pH of bulk solution obtained in step (a) with sodium hydroxide/Hydrochloric acid,
  (c) Adding methionine and monothioglycerol in solution of step (b), and
  (d) Adding Pemetrexed disodium in solution of step (c).

As used herein, the term "pemetrexed" refers to the stable salts, acids and free base forms thereof. The term includes, for example, the free acid, the pharmaceutically acceptable alkali metal, alkaline earth metal, non-toxic metal, ammonium, and substituted ammonium salts, such as for example, the sodium, potassium, lithium, calcium, magnesium, aluminum, zinc, ammonium, trimethylammonium, triethylammonium, monoethanolammonium, triethanolammonium, pyridinium, substituted pyridinium, and the like. The substituted ammonium salts are one especially preferred group of salts.

The disodium salt of Pemetrexed is particularly preferred for use in the present composition. The composition of the invention comprises Pemetrexed disodium 2.5 mg/ml to 50 mg/ml, and more preferably between 20-30 mg/ml.

According to present invention, amount of Pemetrexed is calculated based on absolute amount of Pemetrexed (i.e. free base). For more clarification, 25 mg/ml of Pemetrexed is equivalent 27.57 mg of Pemetrexed disodium and 40 mg/ml of Pemetrexed is equivalent to 44.117 mg of Pemetrexed disodium.

As used herein, the term "Stable formulation" or "Stable composition" means a ready to use aqueous parenteral composition of Pemetrexed disodium wherein amount of any single unknown impurities of Pemetrexed composition is not more than 0.2% after 6 month stability study at 40° C. and 75% RH, and total impurity of Pemetrexed composition is not more than 2% at any time during self-life of the composition.

Specifically, the composition of present invention is stable for at least 18 months when stored at controlled room temperature and total impurity of Pemetrexed composition is not more than 2% at any time during self-life of the composition i.e. till at least 18 months.

As used herein, the term "pharmaceutically acceptable excipients" means a pharmaceutically acceptable formulation carrier, solution or additive to enhance the formulation characteristics. Such additives are well known to the skilled artisan.

A stable, ready to use aqueous parenteral pharmaceutical composition of Pemetrexed is usually solvated in aqueous solvent comprising water for injection.

In preferred embodiments, citric acid has proven to further stabilize the active ingredient and prevent degradation. The citrate or citric acid is preferably added about 10 to 20 mg citric acid anhydrous. Preferably the citric acid or citrate is added and dissolved in solution, with the active compound being present or prior to addition of the active ingredient and then after all ingredients are in place and fully dissolved the complete solution.

In preferred embodiments, antioxidants are to prevent oxidative degradation of Pemetrexed and provide chemical stability to the various parenteral formulations. A preferred antioxidants such as but not limited to methionine, monothioglycerol, L-cysteine, Thioglycolic acid. It follows these antioxidants shall preferably all be soluble and dissolved in the mixing formulation solutions. It may be preferred that the concentration of monothioglycerol is from about 3 mg/ml to about 6 mg/ml. More preferably, the concentration of monothioglycerol is from about 4.0 mg/ml to about 5.0 mg/ml, specifically the concentration of monothioglycerol is 4.4 mg/ml. A preferred concentration of methionine is in some embodiments added to a concentration in the range 0.05-1 mg/ml, such as in the range 0.1-0.5 mg/mL, such as 0.1 or 0.2 mg/mL or 0.5 mg/ml. In a preferred embodiment, concentration of methionine is 0.5 mg/ml.

In a preferred embodiment, antioxidants are a mixture monothioglycerol and methionine; wherein amount of monothioglycerol in the composition of the invention is 3-6 mg/ml and amount of methionine is 0.1-0.5 mg/ml. specifically, the composition comprises monothioglycerol 4.4 mg/ml and methionine 0.5 mg/ml. In any case amount of antioxidants does not exceed 6 mg/ml in the composition of present invention.

In one embodiment of the present invention, the ready to use aqueous parenteral pharmaceutical composition of Pemetrexed has a pH between 6-9 and more preferably between 7-8.5. The pH of such ready to use pharmaceutical compositions of Pemetrexed may be adjusted with a pharmacologically acceptable pH adjusting agent such as an acid, base, buffer or their combination thereof.

In an embodiment of the present invention the pH adjusting agent is hydrochloric acid or sodium hydroxide, or combination thereof.

In another embodiment of the present invention, so as to minimize oxidation of the sensitive material it is also desirable to remove headspace oxygen from the sealable vessel as quickly as possible. This may be aided by, for example, purging the sealable container with a gas which is substantially oxygen-free, or substantially moisture free, or substantially oxygen and moisture free before, during or after step, or any combination thereof. Purging can be expected to reduce the oxygen level in the sealable container to a level of from about 0.5% to about 10%, typically about 5% or lower, depending on the efficiency of flushing and how quickly the container is sealed after flushing.

The gas used for purging the sealable container may be any appropriate inert gas known to those in the art, the most commonly used gases being argon, helium or nitrogen, or mixtures thereof. However, the most preferred inert gas is nitrogen.

The stable pharmaceutical composition of the present invention is analyzed by HPLC method. The method of analysis by HPLC is well known in the art.

In other embodiments, the process may comprise the following: about 70% of total water is loaded in dissolution tank, after addition of citric acid, which may be dissolved, stirred until full dissolution. pH is adjusted to a desired range/value, typically within a range from 7.0 to 8.5, antioxidants are added and solution is stirred to dissolve, Pemetrexed disodium is added to solution stirred to dissolve it and the volume adjusted to full volume by adding remaining water. The solution is filtered. The solution is filled in suitably sized vials with nitrogen flushing. These may be clear vials which are preferably sealed under nitrogen.

The present invention addresses the need for a pharmaceutically stable ready to use Pemetrexed formulation having both physical and chemical stability i.e. color stability and acceptable shelf life stability with regard to retaining the solution dosage form and avoiding unacceptable degradation to undesired related substances. Finally, the formulations provided herein do not require the addition of any preservative, other than the antioxidants, in order to retain the desired concentration and stability.

The stable, ready to use aqueous parenteral composition of present invention is preferably provided in one-dose vials, with sufficient total amount of the active ingredient for a single patient dose, this means that each vial is for single use. The stable, ready to use aqueous parenteral composition of Pemetrexed of the invention does not require reconstitution which provides added advantage to healthcare providers.

EXAMPLES

The present invention has been described by way of example only, and it is to be recognized that modifications thereto falling within the scope and spirit of appended claims, and which would be obvious to a person skilled in the art based upon the disclosure herein, are also considered to be within the scope of this invention.

Example 1: Ready to Use Aqueous Parenteral Compositions of Pemetrexed with Single Antioxidant

| Sr.no. | Ingredients | Example 1 Single antioxidant - Not stable - Not according to the invention mg/mL |
|---|---|---|
| 1 | Pemetrexed Disodium | 44.117* |
| 2 | Monothioglycerol | 2.4 |
| 5 | Sodium hydroxide | q.s. to pH: 7.5 |
| 6 | Hydrochloric acid | q.s. to pH: 7.5 |
| 7 | Water for Injection | q.s. |
| 8 | Nitrogen gas | q.s. to sparge |

*44.117 mg of Pemetrexed disodium eq. to 40 mg of Pemetrexed

Process for Preparation of Composition of Pemetrexed (Single Antioxidant):

Transfer 70% of Batch size equivalent WFI (20-25° C.) in to SS vessel. Sparge nitrogen gas for 60 minute & then continued throughout manufacturing process. Adjust the pH of bulk solution to 7.5 with Sodium hydroxide. Add monothioglycerol and stir to dissolve it. Add Pemetrexed Disodium API and stir to dissolve it. If required, adjust the pH of bulk solution to 7.5 with Sodium hydroxide/Hydrochloric acid. Make up final volume with Water for Injection. Filter the solution with 0.22 micron filters (pre filter & sterilizing grade filter) and fill in vials and stopper after Nitrogen gas flushing in head space.

Stability Study of Example 1

A formulation of Example 1 were stored at different temperatures for varying time periods and impurities were assayed with HPLC assay, the values are estimated concentrations as percentage based on initial content of active ingredient (100%). The samples are stored at 2-8° C., 25° C., 30° C. and 40° C., for time periods of 1 month, 2 months, 3 months, 6 months, 12 months.

TABLE 1

| Stability study condition | pH | single unknown impurity | Total Impurities | Assay |
|---|---|---|---|---|
| 2-8° C., 6M | 7.30 | 0.690 | 1.590 | 103.00 |
| 2-8° C., 12M | 7.00 | 0.785 | 1.655 | 104.50 |

TABLE 1-continued

| Stability study condition | pH | single unknown impurity | Total Impurities | Assay |
|---|---|---|---|---|
| 25° C., 1M | 7.30 | 0.636 | 1.150 | 103.30 |
| 25° C., 2M | 7.30 | 0.712 | 1.409 | 104.30 |
| 25° C., 3M | 7.20 | 0.744 | 1.472 | 104.40 |
| 25° C., 6M | 7.00 | 0.738 | 1.821 | 102.80 |
| 25° C., 12M | 7.10 | 0.888 | 2.126 | 103.90 |
| 30° C., 6M | 7.20 | 0.898 | 2.175 | 102.90 |
| 30° C., 12M | 7.00 | 0.956 | 2.237 | 101.00 |
| 40° C., 1M | 7.20 | 0.611 | 1.242 | 103.50 |
| 40° C., 2M | 7.30 | 0.832 | 1.726 | 104.50 |
| 40° C., 3M | 7.40 | 0.857 | 1.784 | 103.60 |
| 40° C., 6M | 7.10 | 0.995 | 2.336 | 101.70 |

From the stability data provided in the above mentioned Table, it was found that total impurity levels beyond the accepted value. So this formulation cannot be considered as stable for long period of time.

Examples: Ready to Use Aqueous Parenteral Compositions of Pemetrexed with Mixture of Antioxidants

| Sr.no. | Ingredients | Example 2 Mixture of antioxidants - Not stable - Not according to the invention mg/mL | Example 3 Mixture of antioxidants - stable - according to the present invention mg/mL |
|---|---|---|---|
| 1 | Pemetrexed Disodium | 27.57* | 27.57* |
| 2 | Monothioglycerol | 2.4 | 4.4 |
| 3 | Citric acid anhydrous | 10 | 15 |
| 4 | Methionine | 0.5 | 0.5 |
| 5 | Sodium hydroxide | q.s. to pH: 7.5 | q.s. to pH: 7.5 |
| 6 | Hydrochloric acid | q.s. to pH: 7.5 | q.s. to pH: 7.5 |
| 7 | Water for Injection | q.s. to 1 mL | q.s. to 1 mL |
| 8 | Nitrogen gas | q.s. to sparge | q.s. to sparge |

*27.57 mg of Pemetrexed disodium eq. to 25 mg Pemetrexed

Process for Preparation of Composition of Pemetrexed (Mixture of Antioxidants):

Transfer 70% of Batch size equivalent WFI (20-25° C.) in to SS vessel. Sparge nitrogen gas for 60 minute & then continued throughout manufacturing process. Add citric acid anhydrous in above WFI and stir to dissolve it. Adjust the pH of bulk solution to 7.5 with Sodium hydroxide. Add methionine stir to dissolve it. Add monothioglycerol and stir to dissolve it. Add Pemetrexed Disodium API and stir to dissolve it. If required, adjust the pH of bulk solution to 7.5 with Sodium hydroxide/Hydrochloric acid. Make up final volume with Water for Injection. Filter the solution with 0.22 micron filters (pre filter & sterilizing grade filter) and fill in vials and stopper after Nitrogen gas flushing in head space.

Stability Study of Example 2

A formulation of Example 2 were stored at different temperatures for varying time periods and impurities were assayed with HPLC assay, the values are estimated concentrations as percentage based on initial content of active ingredient (100%). The samples are stored at 2-8° C., 25° C., for time periods of 1 month, 3 months, and 6 month.

TABLE 2

| Stability study condition | pH | single unknown impurity | Total Imp | Assay |
|---|---|---|---|---|
| 1M - 2-8° C. | 7.60 | 0.040% | 0.192% | 98.3% |
| 3M - 2-8° C. | 7.47 | 0.043% | 0.230% | 98.3% |
| 6M - 2-8° C. | 7.35 | 0.046% | 0.281% | 99.2% |
| 1M - 25° C., 60% RH | 7.53 | 0.056% | 0.356% | 98.6% |
| 3M - 25° C., 60% RH | 7.57 | 0.170% | 0.708% | 97.4% |
| 6M - 25° C., 60% RH | 7.46 | 0.395% | 0.958% | 99.1% |

From the stability data provided in the above mentioned Table, it was found an Individual major impurity levels beyond the accepted value. So this formulation cannot be stable for long period of time. This formulation fails to comply specification at 6M 25° C./60% RH for single unknown impurity.

Stability Study of Example 3

A formulation of Example 3 were stored at different temperatures for varying time periods and impurities were assayed with HPLC assay, the values are estimated concentrations as percentage based on initial content of active ingredient (100%). The samples are stored at 2-8° C., 25° C. and 40° C., for time periods of 1 month, 2 months, 3 months, 6 months and 12 months.

TABLE 3

| Stability study condition | pH | Single unknown impurity | Total Imp | Assay |
|---|---|---|---|---|
| 3M - 2-8° C. | 7.42 | 0.070% (0.91 RRT) | 0.534% | 101.6% |
| 6M - 2-8° C. | 7.40 | 0.074% (0.91 RRT) | 0.793% | 101.5% |
| 1M - 25° C., 60% RH | 7.61 | 0.071% (0.93 RRT) | 0.744% | 101.2% |
| 2M - 25° C., 60% RH | 7.45 | 0.069% (0.92 RRT) | 0.831% | 103.1% |
| 3M - 25° C., 60% RH | 7.46 | 0.072% (0.91 RRT) | 0.714% | 100.7% |
| 6M - 25° C., 60% RH | 7.40 | 0.075% (0.91 RRT) | 0.799% | 102.0% |
| 1M - 40° C., 75% RH | 7.72 | 0.083% (0.75 RRT) | 1.009% | 101.7% |
| 2M - 40° C., 75% RH | 7.57 | 0.073% (0.91 RRT) | 1.028% | 102.9% |
| 3M - 40° C., 75% RH | 7.59 | 0.077% (1.14 RRT) | 1.115% | 102.2% |
| 6M - 40° C., 75% RH | 7.48 | 0.101% (1.14 RRT) | 1.097% | 101.5% |
| 12M, 25° C., 60% RH | 7.40 | 0.090% (RRT 1.14) | 0.855% | 100.3% |

From the stability data provided in the above mentioned Tables, it can be concluded that the aqueous ready to use formulation of Pemetrexed of the present invention (i.e. example 3) is found stable.

We claim:
1. A stable and ready-to-use aqueous parenteral composition, comprising:
pemetrexed disodium and a mixture of antioxidants, wherein
(a) an amount of pemetrexed disodium is in a range from 2.5 mg/ml to 50 mg/ml, and
(b) an amount of the mixture of antioxidants is in a range from about 3 mg/ml to about 6 mg/ml; and
wherein the antioxidants comprise monothioglycerol and methionine.
2. The stable and ready-to-use aqueous parenteral composition according to claim 1, wherein an amount of the monothioglycerol is in a range from 3 mg/ml to 6 mg/ml, and an amount of the methionine is 0.5 mg/ml.
3. The stable and ready-to-use parenteral composition according to claim 1, wherein an amount of the monothioglycerol is 4.4 mg/ml, and an amount of the methionine is 0.5 mg/ml.
4. The stable and ready-to-use aqueous parenteral composition according to claim 1, wherein the composition has a pH in a range from 6 to 9.
5. The stable and ready-to-use aqueous parenteral composition according to claim 1, wherein the composition further comprises citric acid.
6. The stable and ready-to-use aqueous parenteral composition according to claim 5, wherein an amount of the citric acid is 15 mg/ml.
7. A stable and ready-to-use aqueous parenteral composition comprising pemetrexed disodium, wherein the composition comprises;
(a) pemetrexed disodium in an amount that is in a range from 2.5 mg/ml to 50 mg/ml,
(b) monothioglycerol in an amount that is in a range from 3 mg/ml to 6 mg/ml,
(c) methionine in an amount of 0.5 mg/ml, and
(d) citric acid,
wherein a pH of the composition is in a range from 7 to 8.5.
8. A process for preparing the stable and ready-to-use aqueous parenteral composition according to claim 7, wherein the process comprises:
(a) adding citric acid in water for injection,
(b) adjusting a pH of a bulk solution obtained in (a) with sodium hydroxide or hydrochloric acid,
(c) adding methionine and monothioglycerol in the solution of (b), and
(d) adding pemetrexed disodium in the solution of (c).

* * * * *